(12) United States Patent
Takagi et al.

(10) Patent No.: US 7,328,807 B2
(45) Date of Patent: Feb. 12, 2008

(54) METHOD AND DEVICE FOR CLASSIFYING FINE PARTICLES

(75) Inventors: Seiichi Takagi, Minamiashigara (JP); Kazuki Inami, Ashigarakami-gun (JP); Tetsuo Ohta, Minamiashigara (JP)

(73) Assignee: Fuji Xerox Co., Ltd., Tokyo (JP)

( * ) Notice: Subject to any disclaimer, the term of this patent is extended or adjusted under 35 U.S.C. 154(b) by 4 days.

(21) Appl. No.: 11/113,095

(22) Filed: Apr. 25, 2005

(65) Prior Publication Data

US 2006/0070921 A1 Apr. 6, 2006

(30) Foreign Application Priority Data

Sep. 22, 2004 (JP) ............................ 2004-276164
Feb. 10, 2005 (JP) ............................ 2005-035038

(51) Int. Cl.
*B03B 5/00* (2006.01)
*B03D 1/00* (2006.01)

(52) U.S. Cl. .................... 209/172.5; 172/173; 172/155; 172/156; 172/162; 172/163

(58) Field of Classification Search ................ 209/172, 209/172.5, 173, 155
See application file for complete search history.

(56) References Cited

U.S. PATENT DOCUMENTS 4,424,065 A * 1/1984 Langhoff et al. ......... 48/197 R
5,875,899 A * 3/1999 Nishiyama .................. 209/156
5,947,299 A * 9/1999 Vazquez et al. ............ 209/157
5,971,158 A * 10/1999 Yager et al. ................ 209/155

FOREIGN PATENT DOCUMENTS

JP A 2004-154747 6/2004

OTHER PUBLICATIONS

Megumi Nakajima et al., N201, "Development of a continuous Particle Separation Method by Using the Microchannel Laminar flow System", Preprints of 69th Annual Meeting by Society of chemical Engineers, Japan, with translation.
Shinichi Ookawara et al., "Study of Particle Behavior in Micro-Separator/Classifier Using Euler-Lagrange Method", Preprints of 69th Annual Meeting by Society of chemical Engineers, Japan, with translation.

* cited by examiner

*Primary Examiner*—Patrick Mackey
*Assistant Examiner*—Terrell Matthews
(74) *Attorney, Agent, or Firm*—Oliff & Berridge, PLC (57) ABSTRACT

The present invention provides a method for classifying fine particles, the method comprising: introducing a fine particle dispersion in which fine particles are dispersed in a liquid medium into an inlet of a microchannel having the inlet and a recovery portion; and delivering the fine particle dispersion, which has been introduced through the inlet, to the recovery portion in laminar flow, wherein delivering the fine particle dispersion includes classifying the fine particles using the difference in sedimentation speed or floatation speed among the fine particles in the fine particle dispersion. The present invention also provides a device used in the method for classifying fine particles.

8 Claims, 3 Drawing Sheets

METHOD AND DEVICE FOR CLASSIFYING FINE PARTICLES

CROSS-REFERENCE TO RELATED APPLICATION

This application claims priority under 35 USC 119 from Japanese Patent Application Nos. 2004-276164 and 2005-035038, the disclosures of which are incorporated by reference herein.

BACKGROUND OF THE INVENTION

1. Field of the Invention

The present invention relates to a method for classifying fine particles by using microchannels, and a device for classifying fine particles, which device includes microchannels.

2. Description of the Related Art

Methods for classifying fine particles are categorized into dry methods and wet methods. High accuracy is obtained in dry methods since the difference in specific gravity between a fluid and fine particles is large. In wet methods, although the difference in specific gravity between a liquid and fine particles is small, classification accuracy with respect to fine particles is high because fine particles are easily dispersed in a liquid. A classification device generally includes a rotor in a revolving portion and a stator in a stationary portion of the device, and classifies fine particles by balancing centrifugal force and inertia force. Because of the rotor, however, the classification device has a drawback in that contamination occurs due to abrasion of the rotor, which needs to be removed by cleaning. Further, while dry classifiers which use the Coanda effect and do not have rotors have been commercialized, efficient wet classifiers have not been found. In recent years, various research has been made into performing chemical reactions, unit operations or the like in micrometers, and methods and devices for classifying fine particles efficiently without causing contamination have been studied.

As a method for classifying fine particles, a method is proposed in which the mere introduction of fine particles into a micro-channel enables classification thereof in a horizontal direction in which the fine particles flow. (See, for example, Japanese Patent Application Laid-Open (JP-A) No. 2004-154747, and N201, "Development of Method for Classifying Fine Particles Continuously by Using a Microchannel Laminar Flow System", Preprints of $69^{th}$ Annual Meeting by Society of Chemical Engineers, Japan.) In this method, a microchannel (pinched channel) having a tapered portion, where the channel is locally narrower, is used, and a profile of the characteristic flow of fine particles in the microchannel is utilized. It is reported that by this method separation of fine particles with a particle size of 15 μm from fine particles with a particle size of 30 μm is possible. This method, however, has a drawback in that the size of the channel is limited, thereby limiting the particle size. This method also has a drawback in that the amount of particles which can be introduced into the flow is small, thereby making the method inefficient.

Also proposed as a method for classifying fine particles is a separation and classification method, in which a fine particle dispersion is introduced through an inlet into an arc-shaped microchannel having a square cross section, and centrifugal force and lift are used with relation to the flow rate of a fluid and the difference in specific gravity between the fluid and fine particles. (See, for example, N202, "Study on Behavior inside Microseparation Classifier in Accordance with the Euler-Lagrange Method", Preprints of $69^{th}$ Annual Meeting by Society of Chemical Engineers, Japan.) Since centrifugal force is used in this method, the larger the difference in specific gravity, the better the classification performance. In the case of fine particles with a small particle size, however, the difference in specific gravity between the fluid and the fine particles is small. Thus, these fine particles are uniformly dispersed in the fluid due to vortex flow in a cross-sectional direction generated by the centrifugal force. For this reason, classification is impossible.

These proposed methods have low classification efficiency and are limited in size and the amount of particles in the flow.

SUMMARY OF THE INVENTION

In view of the above-described drawbacks, the present invention provides a method for classifying fine particles, which method has high classification efficiency and classification accuracy, does not cause contamination with abrasion components, and can classify fine particles in a dispersion while the dispersion flows stably. The present invention also provides a device for classifying fine particles, which device can be continuously used for a long period of time, does not cause contamination with abrasion components and has high classification efficiency and classification accuracy.

Specifically, a first aspect of the present invention is a method for classifying fine particles, the method comprising: introducing a fine particle dispersion in which fine particles are dispersed in a liquid medium into an inlet of a microchannel having the inlet and a recovery portion; and delivering the fine particle dispersion, which has been introduced through the inlet, to the recovery portion in laminar flow, wherein delivering the fine particle dispersion includes classifying the fine particles using the difference in sedimentation speed or floatation speed among the fine particles in the fine particle dispersion.

A second aspect of the present invention is a method for classifying fine particles according to the first aspect, wherein the fine particles are selected from the group consisting of resin fine particles, inorganic fine particles, metal fine particles and ceramic fine particles.

A third aspect of the present invention is a method for classifying fine particles according to the first aspect, wherein the volume average particle size is in the range of from 0.1 μm to 1000 μm.

A fourth aspect of the present invention is a method for classifying fine particles according to the first aspect, wherein the content of the fine particles in the fine particle dispersion is in the range from 0.1 to 40% by volume.

A fifth aspect of the present invention is a method for classifying fine particles, the method comprising: introducing a fine particle dispersion in which fine particles are dispersed in a liquid medium into a first inlet of a microchannel having inlets and a recovery portion, and introducing a fluid into a second inlet of the microchannel; and delivering the fine particle dispersion and the fluid, which have been introduced through the inlets, to the recovery portion in laminar flow, such that the fine particle dispersion and the fluid contact at the interface therebetween, wherein delivering the fine particle dispersion includes classifying the fine particles using the difference in sedimentation speed or floatation speed among the fine particles in the laminar flow of the fine particle dispersion and the fluid.

A sixth aspect of the present invention is a method for classifying fine particles according to the fifth aspect, wherein the fine particles are selected from the group consisting of resin fine particles, inorganic fine particles, metal fine particles and ceramic fine particles.

A seventh aspect of the present invention is a method for classifying fine particles according to the fifth aspect, wherein the volume average particle size is in the range of from 0.1 µm to 1000 µm.

An eighth aspect of the present invention is a method for classifying fine particles according to the fifth aspect, wherein the content of the fine particles in the fine particle dispersion is in the range from 0.1 to 40% by volume.

A ninth aspect of the present invention is a device for classifying fine particles in a fine particle dispersion in which fine particles are dispersed in a liquid medium, the device comprising: an introducing portion having an introducing channel for introducing the fine particle dispersion; a classifying portion which is disposed substantially horizontally and classifies the fine particles by causing the fine particles to be sedimented or floated in laminar flow; and a recovery portion having recovery channels which recover the classified fine particles.

A tenth aspect of the present invention is a device for classifying fine particles according to the ninth aspect, wherein the recovery portion includes a plurality of recovery channels.

An eleventh aspect of the present invention is a device for classifying fine particles according to the tenth aspect, wherein the plurality of recovery channels are disposed at different positions in a gravitational direction.

A twelfth aspect of the present invention is a device for classifying fine particles according to the ninth aspect, wherein the introducing portion having at least two introducing portions, which include a first introducing portion having an introducing channel for introducing the fine particle dispersion, and a second introducing portion having an introducing channel for introducing a fluid containing no fine particles to be classified.

A thirteenth aspect of the present invention is a device for classifying fine particles according to the ninth aspect, wherein, when in the fine particle dispersion introducing channel as viewed from above A is the maximum inner dimension of a communicating portion in a horizontal direction orthogonal to a direction in which the fine particle dispersion flows, and in the classifying portion as viewed from above B is the maximum inner dimension of the classifying portion in a horizontal direction orthogonal to a direction in which the fine particle dispersion and a fluid flow in a laminar flow, a value obtained by dividing A by B (A/B) is no more than 0.949.

A fourteenth aspect of the present invention is a device for classifying fine particles according to the ninth aspect, wherein the introducing portion has an opening for introducing the fine particle dispersion, one end of which is disposed above the classifying channel in the gravitational direction, and the other end of which is connected via a communicating portion to an upper surface of the classifying channel, and the classifying portion which is disposed substantially horizontally and classifies the fine particles by causing the fine particles to be sedimented in laminar flow.

A fifteenth aspect of the present invention is a device for classifying fine particles according to the ninth aspect, wherein the introducing portion has an opening for introducing the fine particle dispersion, one end of which is disposed below the classifying channel in the gravitational direction, and the other end of which is connected via a communicating portion to a lower surface of the classifying channel, and the classifying portion which is disposed substantially horizontally and classifies the fine particles by causing the fine particles to be floated in laminar flow.

BRIEF DESCRIPTION OF THE DRAWINGS

Preferred embodiments of the present invention will be described in detail based on the following figures, wherein.

DETAILED DESCRIPTION OF THE INVENTION

The present invention can provide a method for classifying fine particles, the method comprising: introducing a fine particle dispersion in which fine particles are dispersed in a liquid medium into an inlet of a microchannel having the inlet and a recovery portion; and delivering the fine particle dispersion, which has been introduced through the inlet, to the recovery portion in laminar flow, wherein delivering the fine particle dispersion includes classifying the fine particles using the difference in sedimentation speed or floatation speed among the fine particles in the fine particle dispersion.

The present invention also can provide a device for classifying fine particles in a fine particle dispersion in which fine particles are dispersed in a liquid medium, the device comprising: an introducing portion having an introducing channel for introducing the fine particle dispersion; a classifying portion which is disposed substantially horizontally and classifies the fine particles by causing the fine particles to be sedimented or floated in laminar flow; and a recovery portion having recovery channels which recover the classified fine particles.

First Method and Device for Classifying Fine Particles

A first embodiment of a first method for classifying fine particles according to the present invention is a method for classifying fine particles, the method comprising: introducing a fine particle dispersion in which fine particles are dispersed in a liquid medium into an inlet of a microchannel having the inlet and a recovery portion; and delivering the fine particle dispersion, which has been introduced through the inlet, to the recovery portion in laminar flow, wherein delivering the fine particle dispersion includes classifying the fine particles using the difference in sedimentation speed among the fine particles in the fine particle dispersion. This method is applied to a case in which the specific gravity of the fine particles is larger than that of a liquid medium, which is a dispersion medium of the fine particle dispersion.

The first embodiment of the first method for classifying fine particles according to the present invention is a method in which microchannels are used. A microreactor with channels having a width of several micrometers to several thousand micrometers is suitably used as a device having microchannels. The microreactor used in the present invention is a reactor having multiple flow paths (channels) having dimensions in micrometers. Since the channels of the microreactor have dimensions in micrometers, both the dimensions and flow rates of the channels are small, and the Reynolds number of the channels is 2300 or less. Thus, the reactor having the channels having dimensions in micrometers is a device in which laminar flow is predominant, rather than an ordinary reactor in which turbulent flow is predominant.

The Reynolds number (Re) is represented by the equation: $Re=uL/v$, wherein u represents the flow rate, L represents the characteristic length, and v represents the kinematic viscosity coefficient. When this value is about 2300 or less, laminar flow is predominant.

In the device in which laminar flow is predominant as described above, when fine particles in the fine particle dispersion are heavier than the liquid medium, which is the dispersion medium, the fine particles are sedimented in the liquid medium. The sedimentation speed of the fine particles at that time varies with the specific gravity or size of the fine particles. In the first embodiment of the first method for classifying fine particles of the present invention, the difference in sedimentation speed is used for the classification of the fine particles. Particularly, when the fine particles have different particle sizes, the sedimentation speed is proportional to a square value of the particle size. The larger the size of the fine particles, the faster the sedimentation of the fine particles. The first embodiment of the first method for classifying fine particles according to the present invention is suitable for classifying fine particles of different particle sizes.

When turbulent flow of the fine particle dispersion is formed due to a large cross-sectional size of the channel, a position at which the fine particles are sedimented changes. In this case, classification of the fine particles is basically impossible.

A second embodiment of the first method for classifying fine particles according to the present invention is a method for classifying fine particles, comprising: introducing a fine particle dispersion in which fine particles are dispersed in a liquid medium into a first inlet of a microchannel having inlets and a recovery portion, and introducing a fluid into a second inlet of the microchannel; and delivering the fine particle dispersion and the fluid, which have been introduced through the inlet, to the recovery portion in laminar flow, wherein delivering the fine particle dispersion includes classifying the fine particles using the difference in sedimentation speed among the fine particles in the laminar flow of the fine particle dispersion and the fluid. The second embodiment of the first method for classifying fine particles according to the present invention is applied to a case in which the specific gravity of the fine particles is larger than that of a liquid medium, which is a dispersion medium of the fine particle dispersion. As in the first embodiment of the first method for classifying fine particles, the microreactor with channels having a width of several micrometers to several thousand micrometers is suitably used. Namely, the fine particles are classified in the device in which laminar flow is predominant.

In the second embodiment of the first method for classifying fine particles according to the present invention, the fine particle dispersion is introduced into the fluid. Since the fine particles are heavier than the fluid and the liquid medium serving as the dispersion medium, the fine particles are sedimented in the laminar flow of the fluid and the fine particle dispersion. At that time, the difference in sedimentation speed, which is caused by the fine particles being different from one another in specific gravity or particle size, can be used for the classification of the fine particles.

The second embodiment of the first method for classifying fine particles is the same as the first embodiment except that the fine particles are not sedimented, but the fine particles are introduced into the fluid and the fine particles are caused to be sedimented in the laminar flow of the fluid and the fine particle dispersion. Preferred aspects of the second embodiment of the first method for classifying fine particles are the same as those of the first embodiment as well.

The first and second embodiments of the first method for classifying fine particles (hereinafter may be collectively referred to as the "first method for classifying fine particles") can be carried out by using a first device for classifying fine particles of the present invention, which will be described below.

The first device for classifying fine particles according to the present invention is a device for classifying fine particles in a fine particle dispersion in which fine particles are dispersed in a liquid medium, the device comprising: a first introducing portion having a first introducing channel for introducing the fine particle dispersion; a classifying portion which is disposed substantially horizontally and classifies the fine particles by causing the fine particles to be sedimented in laminar flow; and a recovery portion having recovery channels which recover the classified fine particles. The first device for classifying fine particles may further comprise a second introducing portion having a second introducing channel, which is disposed substantially horizontally, for introducing a fluid.

Further, the first device for classifying fine particles of the present invention preferably comprises a plurality of recovery channels which are preferably connected to the classifying channel at different positions thereof in a gravitational direction, at different positions in a direction in which the fine particle dispersion (or a laminar flow of the fine particle dispersion and the fluid) flows, or at different positions in both the gravitational direction and the direction in which the fine particle dispersion flows. It is far more preferable that the plural recovery channels are connected to the classifying channel at different positions thereof in the gravitational direction.

Figure 1:
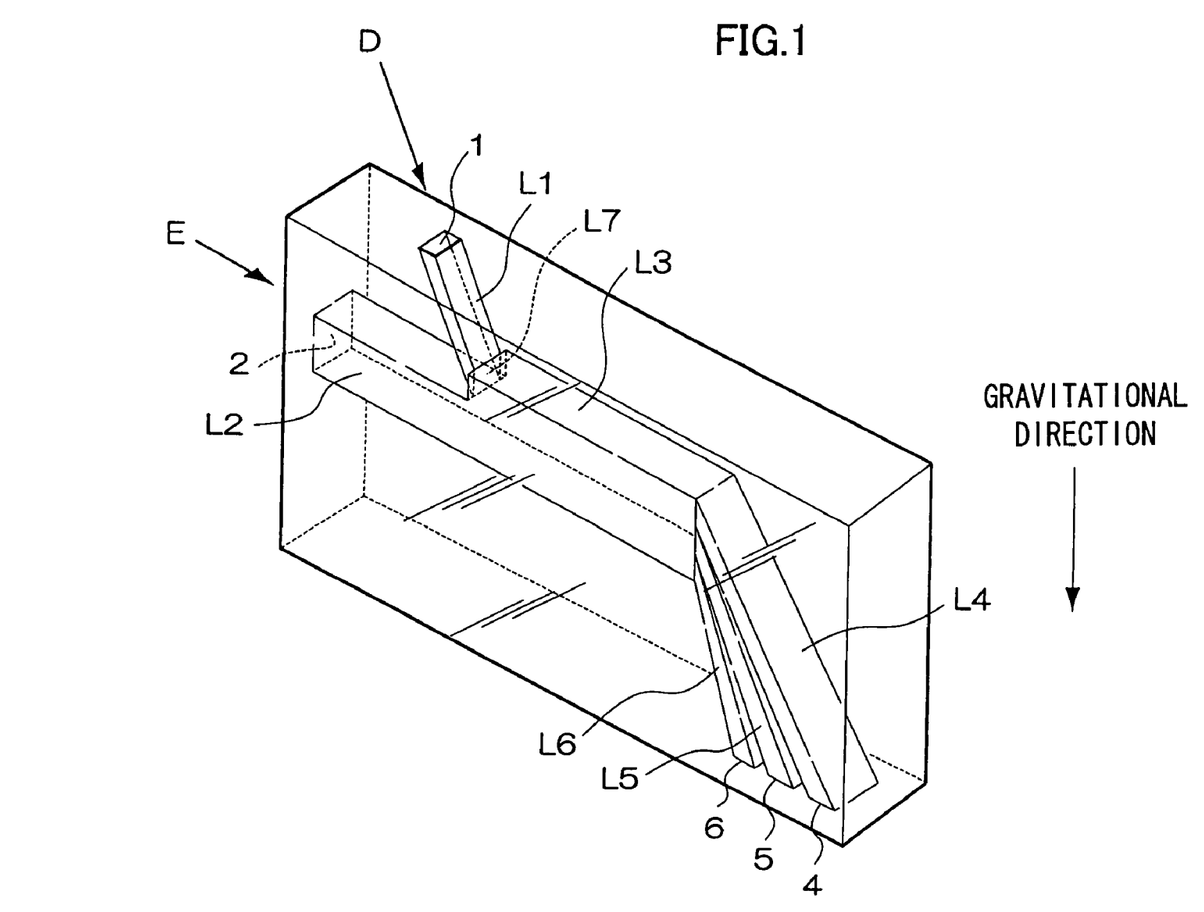
FIG. 1 is a schematic structural drawing showing an example of a first device for classifying fine particles of the present invention.

An example of the first device for classifying fine particles will be described with reference to FIG. 1. FIG. 1 is a schematic structural drawing showing an example of the first device for classifying fine particles.

The first device for classifying fine particles shown in FIG. 1 is a microreactor with channels having a width of several micrometers to several thousand micrometers, as described above. The microreactor includes a classifying channel L3, a fine particle dispersion introducing channel L1, recovery channels L4, L5 and L6, and a fluid introducing channel L2. The classifying channel L3 is disposed substantially horizontally and classifies fine particles in a laminar flow of a fine particle dispersion D and a fluid E (or fine particles in the fine particle dispersion D when the fluid introducing channel L2 with an opening 2 is not provided, as will be described later) by causing the fine particles to be sedimented in laminar flow. The fine particle dispersion introducing channel L1 has an opening (inlet) 1 at an end thereof for introducing the fine particle dispersion D, which opening is located above the classifying channel 3 in a gravitational direction, and the other end of the fine particle dispersion introducing channel L1 is connected via a communicating portion L7 to a side of the classifying channel L3 opposite to the side at which the recovery channels L4, L5 and L6 are disposed, such that the fine particle dispersion D introduced through the opening 1 is guided to the classifying channel L3. The recovery channels L4, L5 and L6 respectively have, at ends thereof, openings (recovery portions) 4, 5 and 6 which are located below the classifying channel L3 in the gravitational direction, and the other ends of the recovery channels L4, L5 and L6 are connected to the downstream end of the classifying channel L3, such that the classified fine particles are recovered. The other ends of the recovery channels L4, L5 and L6 are provided at positions of different heights in the gravitational direction. The fluid introducing channel L2 is disposed substantially horizontally and has an opening 2 at an end thereof for introducing the fluid E containing no fine particles to be classified, and the other end of the fluid introducing channel L2 is connected to the end of the classifying channel L3 opposite to the downstream end connected to the recovery channels L4, L5 and L6, such that the fluid introduced through the opening 2 is introduced into the classifying channel L3. The classifying channel L3 herein refers to a region in which the fine particles are classified. In the first device for classifying fine particles of the present invention, the classifying channel L3 refers to a region extending from the communicating portion L7 to inlets of the recovery channels (the recovery channels L4, L5 and L6 in the device shown in FIG. 1).

Classification of the fine particles by using the device for classifying the fine particles shown in FIG. 1 is carried out as follows. The fine particle dispersion D is introduced through the opening 1. The fine particle dispersion D thus introduced passes through the fine particle dispersion introducing channel L1 and the communicating portion L7, and is guided to the classifying channel L3. The fluid E is introduced through the opening 2. The fluid E introduced passes through the fluid introducing channel L2 and is guided to the classifying channel L3. The fine particle dispersion D and the fluid E introduced into the classifying channel L3 move downstream along the classifying channel L3 in the state of laminar flow. While the fine particle dispersion D and the fluid E introduced into the classifying channel L3 move downstream along the classifying channel L3, the fine particles in the fine particle dispersion D are gradually sedimented because the specific gravity thereof is larger than that of the liquid medium in the fine particle dispersion D and the fluid E. Since the sedimentation speed of the fine particles varies according to the density or size of the fine particles, the fine particles are distributed at different heights in the gravitational direction when the fine particles have reached the downstream end of the classifying channel L3. Thus, the fine particles flow into the recovery channels L4, L5 and L6 located at different heights in the gravitational direction, whereby the classified fine particles can be obtained through the openings 4, 5 and 6.

When the first device for classifying fine particles of the present invention does not have the fluid introducing channel L2, only the fine particle dispersion D is introduced into the fine particle dispersion introducing channel L1. While only the fine particle dispersion D guided along the classifying channel L3 moves downstream in the state of laminar flow, the fine particles in the dispersion D are sedimented. The fine particles are distributed at different heights in the gravitational direction due to their different sedimentation speeds when they have reached the downstream end of the classifying channel L3. The fine particles flow into the recovery channels L4, L5 and L6 provided at different heights in the gravitational direction, whereby the classified fine particles can be obtained through the openings 4, 5 and 6.

When the first device for classifying fine particles of the present invention does not have the opening 2 or the fluid introducing channel L2, the device is used in the above-described first embodiment of the first method for classifying fine particles of the present invention. When the first device for classifying fine particles of the present invention has the opening 2 and the fluid introducing channel L2, the device is used in the above-described second embodiment of the first method for classifying fine particles of the present invention.

In the first device for classifying fine particles of the present invention, the opening 1 is not located below the classifying channel L3 in the gravitational direction. Therefore, the fine particle dispersion introducing channel L1 has an angle of 0° to less than 180° with respect to a top surface of the classifying channel L3 in the gravitational direction.

Further, in the first device for classifying fine particles of the present invention, the openings (the openings 4, 5 and 6 in the device shown in FIG. 1) of the respective recovery channels are not located above the classifying channel L3 in the gravitational direction. Therefore, the recovery channels L4, L5 and L6 respectively have an angle of 0° to less than 90° with respect to a bottom surface of the classifying channel L3 in the gravitational direction such that their outlets are located below the classifying channel L3 in the gravitational direction.

Furthermore, the classifying channel L3 and the fluid introducing channel L2 are disposed substantially horizontally (preferably horizontally) in the first device for classifying fine particles of the present invention. "Substantially horizontal" means that the angle with respect to a horizontal direction is 0° to 30°.

The first device for classifying fine particles shown in FIG. 1 includes three recovery channels and three corresponding openings, i.e., the recovery channels L4, L5 and L6 and the openings 4, 5 and 6. The number of the recovery channels, however, is not particularly limited and does not need to be three as in the device shown in FIG. 1. It is preferable that the number of the recovery channels corresponds to the number of types of fine particles to be classified.

When the first device for classifying fine particles includes multiple recovery channels, as in the device for classifying fine particles shown in FIG. 1, the recovery channels L4, L5 and L6 may be connected to the classifying channel L3 at positions of different heights in the gravitational direction, or may be connected to the classifying channel L3 at different positions thereof in a direction in which the fine particle dispersion D (or the laminar flow of the fine particle dispersion D and the fluid E) flows, or at different positions thereof in both the gravitational direction and the direction in which the fine particle dispersion D (or the laminar flow of the fine particle dispersion D and the fluid E) flows. When the recovery channels L4, L5 and L6 are connected to the classifying channel L3 at different positions thereof in the direction in which the fine particle dispersion D (or the laminar flow of the fine particle dispersion D and the fluid E) flows, the fine particles can be classified by using the difference in position at the bottom surface of the classifying channel L3 that the fine particles reach.

In the device for classifying fine particles shown in FIG. 1, the communicating portion L7 is located at the side of the classifying channel L3 opposite to the side at which the recovery channels L4, L5 and L6 are disposed. In the first device for classifying fine particles of the present invention, however, it suffices if the communicating portion L7 is located above the fluid introducing channel L2. The communicating portion L7 may be located at the top surface of the classifying channel L3 at an upstream side thereof.

In the first device for classifying fine particles of the present invention, all of the channels except the fluid introducing channel L2 and the classifying channel L3 (i.e., the fine particle dispersion introducing channel L1 and the recovery channels L4, L5 and L6 in the device for classifying fine particles shown in FIG. 1) have an angle of ±0° to 45°, preferably ±0° to 30°, more preferably ±0° to 15°, and particularly preferably ±0° to 10°, with respect to the gravitational direction (a perpendicular line). If the angle with respect to the gravitational direction exceeds ±45°, the fine particles are easily sedimented in the fine particle dispersion introducing channel L1 or the recovery channels L4, L5 and L6 when the flow rate of the fluid E or the fine particle dispersion D is low. The sedimented fine particles may adhere to the bottom surface of the channel and block the channel.

In the device for classifying fine particles shown in FIG. 1, the fine particle dispersion introducing channel L1, the fluid introducing channel L2, the classifying channel L3 and the recovery channels L4, L5 and L6 each have a rectangular cross section. In the first device for classifying fine particles of the present invention, however, these channels do not need to necessarily have a rectangular cross section.

When the shape of the channel varies according to portions thereof, the "angle with respect to the gravitational direction" described herein refers to an angle formed by the center line of each channel and the gravitational direction.

When the first device for classifying fine particles of the present invention includes the fluid introducing channel L2 having the opening 2, the ratio of an area of the opening 1 to an area of the opening 2 (i.e., the area of the opening 1: the area of the opening 2) is preferably 0.01:1 to 1:1, and more preferably 0.05:1 to 0.5:1, in light of the relationship between the specific gravity of the dispersed fine particles and the specific gravity of the fluid, the flow rate of the fluid, and classification accuracy required.

Figure 2:
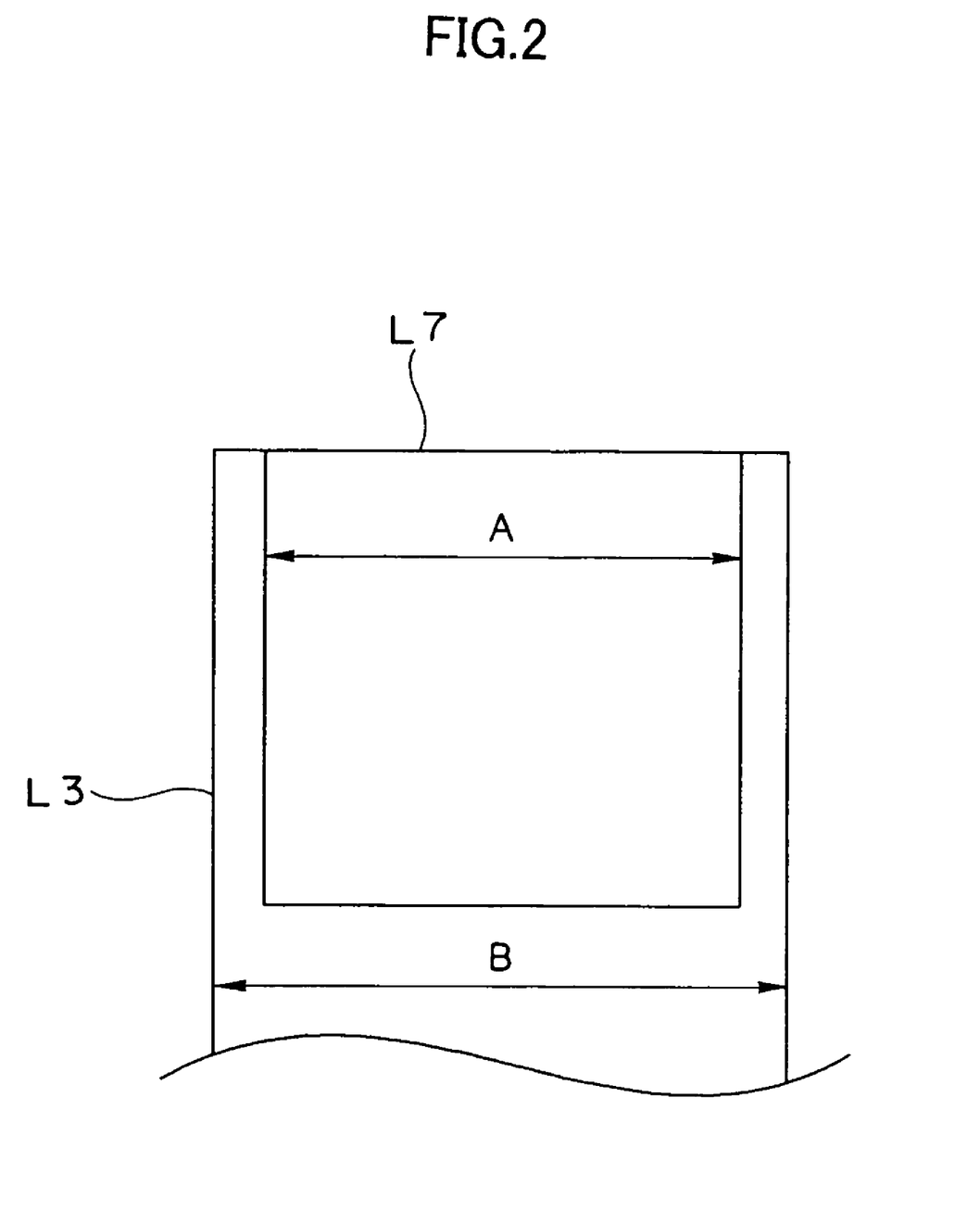
FIG. 2 is a view explaining that inner dimensions of a communicating portion L7 are smaller than those of a classifying channel L3.

Moreover, when the first device for classifying fine particles of the present invention includes the fluid introducing channel L2, the communicating portion L7 preferably has an inner dimension smaller than that of the classifying channel L3, as further shown in FIG. 2. Specifically, when, in the fine particle dispersion introducing channel L1 when viewed from above, A is the maximum inner dimension of the communicating portion L7 in a horizontal direction orthogonal to the direction in which the fine particle dispersion D flows, and, in the classifying channel L3 when viewed above, B is the maximum inner dimension of the classifying channel L3 in a horizontal direction orthogonal to the direction in which the laminar flow of the fine particle dispersion D and the fluid E flows, a value obtained by dividing A by B (A/B) is preferably 0.949 or less, and more preferably 0.4 to 0.9. If the A/B exceeds 0.949, the fine particles flow extremely slow at positions extremely close to inner wall surfaces of the classifying channel L3, whereby sedimentation of the fine particles may become apparently fast. This may cause separation of the fine particles, which is inappropriate for the intended design of the device, and fine particles of small diameter may be mixed and recovered together with fine particles of larger diameters. When the A/B is below 0.4, on the other hand, the efficiency of the fine particle dispersion D introduced may deteriorate.

Further, the first device for classifying fine particles of the present invention is preferably formed so that the center line of the fine particle dispersion introducing channel L1 and the center line of the classifying channel L3 are on the same plane. When these center lines are on the same plane, an effect obtained by the A/B being 0.949 or less becomes more significant.

The fine particle dispersion D and the fluid E are preferably introduced with pressure through the opening 1 and the opening 2, respectively, by injection with microsyringes, rotary pumps, screw pumps, centrifugal pumps, piezopumps or the like.

The flow rate of the fine particle dispersion D in the fine particle dispersion introducing channel L1 is preferably 0.001 to 100 ml/hour, and more preferably 0.01 to 50 ml/hour.

Further, the flow rate of the fluid E in the fluid introducing channel L2 is preferably 0.002 to 1000 ml/hour, and more preferably 0.1 to 500 ml/hour.

The microreactor used in the first device for classifying fine particles of the present invention may be formed of a material in general use, such as metal, ceramic, plastic, glass or the like. It is preferable that the material is appropriately selected depending on the liquid medium to be delivered.

The fine particle dispersion D used in the first method for classifying fine particles, which method is carried out by using the first device for classifying fine particles of the present invention, will now be described.

It is preferable that the fine particle dispersion D is a dispersion in which fine particles having a volume-average particle size of 0.1 to 1000 μm are dispersed in a liquid medium, and the value obtained by subtracting the value of the specific gravity of the liquid medium from the value of the specific gravity of the fine particles is 0.01 to 20.

The fine particles used in the first method for classifying fine particles of the present invention are not particularly limited as long as the volume-average particle size thereof is from 0.1 to 1000 μm. The fine particles may be selected from resin fine particles, inorganic fine particles, metal fine particles, ceramic fine particles and the like.

The volume-average particle size of the fine particles used in the first method for classifying fine particles of the present invention is required to be from 0.1 to 1000 μm, as described above, and is preferably from 0.1 to 500 μm, more preferably from 0.1 to 200 μm, and particularly preferably from 0.1 to 50 μm. If the volume-average particle size of the fine particles is more than 1000 μm, the fine particles in the fine particle dispersion D delivered in the microchannel suitably used in the present invention may block the channel since the average cross-sectional area of the microchannels is from several micrometers to several thousands of micrometers as described above. Further, if the sedimentation speed of the fine particles is too fast, deposits of the fine particles on the bottom of the channel or blockage of the channel may occur. On the other hand, if the volume-average particle size of the fine particles is less than 0.1 μm, the problem of fine particles being deposited hardly arises, but the influence of interaction between the fine particles and the inner wall surfaces increases, resulting in problems such as adhesion of the fine particles onto the inner wall surfaces.

The shape of the fine particles used in the first method for classifying fine particles of the present invention is not particularly limited. However, if the fine particles are of a needle form, and in particular if the long axis thereof is larger than ¼ of the width of the channel, the possibility that the channel gets blocked becomes high. From this perspective, the ratio of the long axis length of the fine particles to the short axis length thereof (that is, the long axis length/the short axis length) is preferably from 1 to 50, and more preferably from 1 to 20. It is desired to select the channel width appropriately in accordance with the particle size and the particle shape.

The type of the fine particles used in the first method for classifying fine particles may be any one of the types listed in the following examples, but are not limited thereto: organic and inorganic crystals or aggregates, such as polymer particles or pigment particles; metal fine particles; and metal compound fine particles such as metal oxide, metal sulfide and metal nitride fine particles.

Specific examples of the polymer fine particles include fine particles made of the following: polyvinyl butyral resin, polyvinyl acetal resin, polyarylate resin, polycarbonate resin, polyester resin, phenoxy resin, polyvinyl chloride resin, polyvinylidene chloride resin, polyvinyl acetate resin, polystyrene resin, acrylic resin, methacrylic resin, styrene/acrylic resin, styrene/methacrylic resin, polyacrylamide resin, polyamide resin, polyvinyl pyridine resin, cellulose-based resin, polyurethane resin, epoxy resin, silicone resin, polyvinyl alcohol resin, casein, vinyl chloride/vinyl acetate copolymer, modified vinyl chloride/vinyl acetate copolymer, vinyl chloride/vinyl acetate/maleic anhydride copolymer, styrene/butadiene copolymer, vinylidene chloride/acrylonitrile copolymer, styrene/alkyd resin, and phenol/formaldehyde resin, and the like.

Examples of the metal or metal compound fine particles include fine particles made of the following: carbon black; a metal such as zinc, aluminum, copper, iron, nickel, chromium, titanium and the like, or alloys thereof; metal oxides such as $TiO_2$, $SnO_2$, $Sb_2O_3$, $In_2O_3$, ZnO, MgO, iron oxide and the like, or any compound thereof; metal nitrides such as silicon nitride and the like; and any combination thereof.

Various processes for producing these fine particles may be used. In many cases, fine particles are produced by synthesis in a liquid medium and subjected to classification. Fine particles may also be produced by mechanically pulverizing a bulk material and dispersing the resulting fine particles in a liquid medium, followed by classification. In this process, the material is often pulverized in the liquid medium and the resulting fine particles are classified directly.

In cases where powder (i.e., fine particles) is produced in a dry process, it is necessary to disperse the powder in a liquid medium before using. The method for dispersing the dry powder in the liquid medium may be a method using a sand mill, a colloid mill, an attritor, a ball mill, a Dyno mill, a high-pressure homogenizer, an ultrasonic disperser, a co-ball mill, a roll mill or the like. At this time, it is preferable to perform the process under conditions where primary particles are not pulverized by the dispersion process.

In the first method for classifying fine particles, the value obtained by subtracting the value of the specific gravity of the liquid medium from the value of the specific gravity of the fine particles is preferably 0.01 to 20, more preferably 0.05 to about 11, and far more preferably 0.05 to 4. If the difference obtained by subtracting the value of the specific gravity of the liquid medium from the value of the specific gravity of the fine particles is less than 0.01, sedimentation of the particles may not take place, but if the difference exceeds 20, the sedimentation of the fine particles may occur remarkably, and the fine particles may not be easily delivered.

As the liquid medium used in the first method for classifying fine particles, the liquid medium is preferably used as long as, as described above, the difference obtained by subtracting the value of the specific gravity of the liquid medium from the value of the specific gravity of the fine particles is 0.01 to 20. Examples thereof include water, aqueous media, organic solvent type media and the like.

The water may be ion-exchange water, distilled water, electrolytic ion water or the like. Specific examples of the organic solvent type media include methanol, ethanol, n-propanol, n-butanol, benzyl alcohol, methylcellosolve, ethylcellosolve, acetone, methyl ethyl ketone, cyclohexanone, methyl acetate, n-butyl acetate, dioxane, tetrahydrofuran, methylene chloride, chloroform, chlorobenzene, toluene, xylene and the like, and mixtures of two or more thereof.

In the first method for classifying fine particles of the present invention, the preferred example of the liquid medium varies depending on the type of the fine particles. Preferred examples of the liquid medium for combining with polymer fine particles (the specific gravity thereof being generally from 1.05 to about 1.6) include aqueous solvents, organic solvents (such as alcohols, xylene and the like), acidic or alkaline waters and the like which do not dissolve the fine particles.

Further, preferred examples of the liquid media for combining with the metal or metal compound fine particles (the specific gravity thereof being generally from 2 to about 10) include water, organic solvents (such as alcohols, xylene and the like), and oils which do not oxidize, reduce, or otherwise react with the metal.

In the first method for classifying fine particles of the present invention, more preferred examples of combinations of the fine particles and the liquid media include a combination of polymer fine particles and an aqueous medium, and a combination of metal or a metal compound and a low-viscosity oily medium. Particularly preferable is the combination of polymer fine particles and an aqueous medium.

Preferable examples of the combination of the fine particles and the liquid medium include a combination of styrene/acrylic resin fine particles and an aqueous medium, a combination of styrene/methacrylic resin fine particles and an aqueous medium, and a combination of polyester resin fine particles and an aqueous medium.

In the first method for classifying fine particles of the present invention, the content of the fine particles in the fine particle dispersion is preferably from 0.1 to 40% by volume, and more preferably from 5 to 25% by volume. If the content of the fine particles in the fine particle dispersion is less than 0.1% by volume, problems may occur during recovery of the fine particles. If the content is more than 40% by volume, the possibility that the particles block the channel may increase.

In the present invention, the volume-average particle size of the fine particles is a value measured with a Coulter counter TA-II model (manufactured by Beckman Coulter, Inc.) except when the fine particles have a particle size of 5 μm or less. The volume-average particle size is measured by use of an optimal aperture depending on the particle size level of the fine particles. However, in cases where the fine particles have a particle size of about 5 μm or less, the volume-average particle size is measured with a laser scattering particle size distribution measuring device (trade name: LA-920, manufactured by Horiba, Ltd.).

The specific gravity of the fine particles is measured with a pycnometer (trade name: Ultrapycnometer 1000, manufactured by Yuasa Ionics Co., Ltd.) by gas phase displacement method (pycnometer method).

The specific gravity of any liquid medium is measured with a specific gravity determination kit (trade name: AD-1653) manufactured by A & D Co., Ltd.

In the first method for classifying fine particles of the present invention, the fluid E is a liquid containing no fine particles to be classified. In the present invention, the fluid E is preferably the same as the liquid medium.

Moreover, when the fluid E is different from the liquid medium, the fluid E is preferably selected from the specific examples of the liquid medium described above.

Further, a preferred range of the specific gravity of the fluid E with respect to the fine particles is the same as the preferred range of the specific gravity of the liquid medium with respect to the fine particles.

Second Method and Device for Classifying Fine Particles

A first embodiment of a second method for classifying fine particles according to the present invention comprises: introducing a fine particle dispersion in which fine particles are dispersed in a liquid medium into an inlet of a microchannel having the inlet and a recovery portion; and delivering the fine particle dispersion, which has been introduced through the inlet, to the recovery portion in laminar flow, wherein delivering the fine particle dispersion includes classifying the fine particles using the difference in floatation speed among the fine particles in the fine particle dispersion. This method is applied to a case in which the specific gravity of the fine particles is smaller than that of a liquid medium, which is a dispersion medium.

The first embodiment of the second method for classifying fine particles according to the present invention is a method in which microchannels are used. A microreactor can be preferably used in the same way as in the first embodiment of the first method for classifying fine particles of the present invention. Thus, the first embodiment of the second method for classifying fine particles is carried out in a device for classifying fine particles in which laminar flow is predominant.

In the device in which laminar flow is predominant as described above, when fine particles in the fine particle dispersion are lighter than the liquid medium, which is the dispersion medium, the fine particles float upward in the liquid medium. The floatation speed of the fine particles at that time varies with the specific gravity or the size of the fine particles. In the first embodiment of the second method for classifying fine particles of the present invention, the difference in floatation speed is used for the classification of the fine particles. Particularly, when the fine particles have different particle sizes, the floatation speed is proportional to a square value of the particle size. The larger the size of the fine particles, the faster the floatation of the fine particles. The first embodiment of the second method for classifying fine particles according to the present invention is suitable for classifying fine particles of different particle sizes.

When turbulent flow of the fine particle dispersion is formed due to a large cross-sectional size of the channel, a position at which the fine particles float upward changes. In this case, classification of the fine particles is basically impossible.

A second embodiment of the second method for classifying fine particles according to the present invention is a method for classifying fine particles, comprising: introducing a fine particle dispersion in which fine particles are dispersed in a liquid medium into a first inlet of a microchannel having inlets and a recovery portion, and introducing a fluid into a second inlet of the microchannel; and delivering the fine particle dispersion and the fluid, which have been introduced through the inlet, to the recovery portion in laminar flow, wherein delivering the fine particle dispersion includes classifying the fine particles using the difference in floatation speed among the fine particles in the laminar flow of the fine particle dispersion and the fluid.

The second embodiment of the second method for classifying fine particles according to the present invention is applied to a case in which the specific gravity of the fine particles is smaller than that of a liquid medium, which is a dispersion medium. As in the first embodiment of the second method for classifying fine particles, the microreactor with the channel having a width of several micrometers to several thousand micrometers is suitably used. Namely, the fine particles are classified in the device in which laminar flow is predominant.

In the second embodiment of the second method for classifying fine particles according to the present invention, the fine particle dispersion is introduced into the fluid. Since the fine particles are lighter than the fluid and the liquid medium, the fine particles float upward in the laminar flow of the fluid and the fine particle dispersion. At that time, the difference in floatation speed, which is caused by the fine particles being different from one another in specific gravity or particle size, can be used for the classification of the fine particles.

The second embodiment of the second method for classifying fine particles is the same as the first embodiment except that the fine particles are not allowed to float upwards in the fine particle dispersion, but the fine particles are introduced into the fluid and caused to float upward in the laminar flow of the fluid and the fine particle dispersion. Preferred aspects of the second embodiment of the second method for classifying fine particles are the same as those of the first embodiment as well.

The first and second embodiments of the second method for classifying fine particles (hereinafter may be collectively referred to as the "second method for classifying fine particles") can be carried out by using a second device for classifying fine particles of the present invention, which will be described below.

The second device for classifying fine particles according to the present invention is a device for classifying fine particles in a fine particle dispersion, the device comprising: a first introducing portion having a first introducing channel for introducing the fine particle dispersion; a classifying portion which is disposed substantially horizontally and classifies the fine particles by causing the fine particles to float upward in laminar flow; and a recovery portion having recovery channels which recover the classified fine particles. The second device for classifying fine particles may further comprise a second introducing portion having a second introducing channel, which is disposed substantially horizontally, for introducing a fluid.

Further, the second device for classifying fine particles of the present invention preferably comprises a plurality of recovery channels which are preferably connected to the classifying channel at different positions thereof in a buoyant (gravitational) direction, at different positions in a direction in which the fine particle dispersion (or a laminar flow of the fine particle dispersion and the fluid) flows, or at different positions in both the buoyant direction and the direction in which the fine particle dispersion flows. It is far more preferable that the plural recovery channels are connected to the classifying channel at different positions thereof in the buoyant direction.

Figure 3:
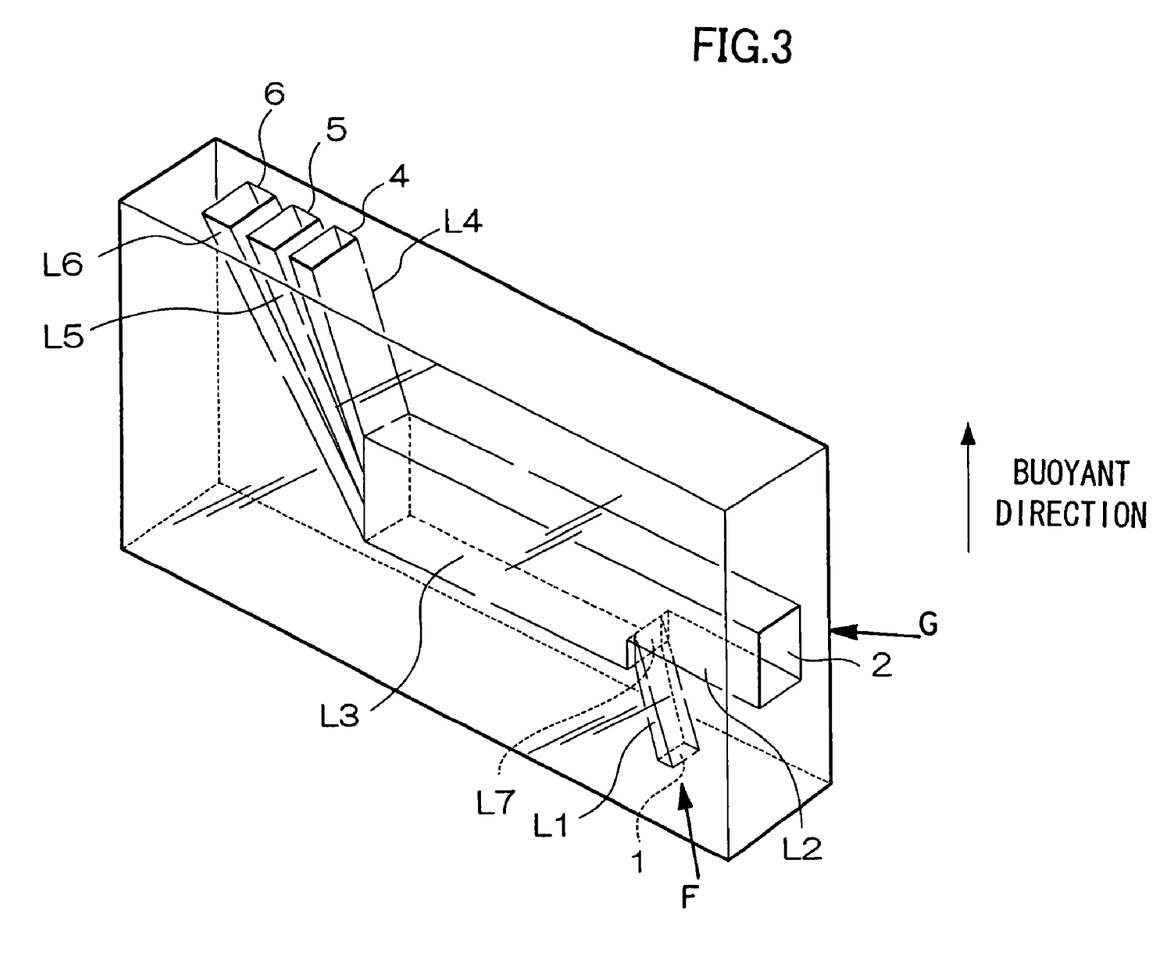
FIG. 3 is a schematic structural drawing showing an example of a second device for classifying fine particles of the present invention.

An example of the second device for classifying fine particles will be described with reference to FIG. 3. FIG. 3 is a schematic structural drawing showing an example of the second device for classifying fine particles.

The second device for classifying fine particles shown in FIG. 3 is a microreactor with channels having a width of several micrometers to several thousand micrometers, as described above. The microreactor includes a classifying channel L3, a fine particle dispersion introducing channel L1, recovery channels L4, L5 and L6, and a fluid introducing channel L2. The classifying channel L3 is disposed substantially horizontally and classifies fine particles in a laminar flow of a fine particle dispersion F and a fluid G (or fine particles in the fine particle dispersion F when the fluid introducing channel L2 with the opening 2 is not provided, as will be described later) by causing the fine particles to float upward in laminar flow. The fine particle dispersion introducing channel L1 has an opening (inlet) 1 at an end thereof for introducing the fine particle dispersion F, which opening is located below the classifying channel 3 in a gravitational direction (buoyant direction), and the other end of the fine particle dispersion introducing channel L1 is connected via a communicating portion L7 to the classifying channel L3, such that the fine particle dispersion F introduced through the opening 1 is guided to the classifying channel L3. The recovery channels L4, L5 and L6 respectively have, at ends thereof, openings (recovery portions) 4, 5 and 6 which are located above the classifying channel L3 in the gravitational direction (buoyant direction), and the other ends of the recovery channels L4, L5 and L6 are connected to the downstream end of the classifying channel L3, such that the classified fine particles are recovered. The other ends of the recovery channels L4, L5 and L6 are provided at positions of different heights in the gravitational direction (buoyant direction). The fluid introducing channel L2 is disposed substantially horizontally and has an opening 2 at an end thereof for introducing the fluid G containing no fine particles to be classified, and the other end of the fluid introducing channel L2 is connected to the end of the classifying channel L3 opposite to the downstream end connected to the recovery channels L4, L5 and L6, such that the fluid introduced through the opening 2 is introduced into the classifying channel L3. The classifying channel L3 herein refers to a region in which the fine particles are classified. In the second device for classifying fine particles of the present invention, the classifying channel L3 refers to a region extending from the communicating portion L7 to inlets of the recovery channels (the recovery channels L4, L5 and L6 in the device shown in FIG. 3).

Classification of the fine particles by using the device for classifying the fine particles shown in FIG. 3 is carried out as follows. The fine particle dispersion F is introduced through the opening 1. The fine particle dispersion F thus introduced passes through the fine particle dispersion introducing channel L1 and the communicating portion L7, and is guided to the classifying channel L3. The fluid G is introduced through the opening 2. The fluid G introduced passes through the fluid introducing channel L2 and is guided to the classifying channel L3. The fine particle dispersion F and the fluid G introduced into the classifying channel L3 move downstream along the classifying channel L3. While the fine particle dispersion F and the fluid G introduced into the classifying channel L3 move downstream along the classifying channel L3, the fine particles in the fine particle dispersion G gradually float upward because the specific gravity thereof is smaller than that of the liquid medium in the fine particle dispersion F and the fluid G. Since the floatation speed of the fine particles varies according to the density or size of the fine particles, the fine particles are distributed at different heights in the gravitational direction when the fine particles have reached the downstream end of the classifying channel L3. Thus, the fine particles flow into the recovery channels L4, L5 and L6 located at different heights, whereby the classified fine particles can be obtained through the openings 4, 5 and 6.

When the second device for classifying fine particles of the present invention does not have the fluid introducing channel L2, only the fine particle dispersion F is introduced into the fine particle dispersion introducing channel L1. While only the fine particle dispersion F guided along the classifying channel L3 moves downstream, the fine particles in the dispersion F float upward. The fine particles are distributed at different heights in the gravitational direction due to their different floatation speeds when they have reached the downstream end of the classifying channel L3. The fine particles flow into the recovery channels L4, L5 and L6 provided at different heights, whereby the classified fine particles can be obtained through the openings 4, 5 and 6.

When the second device for classifying fine particles of the present invention does not have the opening 2 or the fluid introducing channel L2, the device is used in the above-described first embodiment of the second method for classifying fine particles of the present invention. When the second device for classifying fine particles of the present invention has the opening 2 and the fluid introducing channel L2, the device is used in the above-described second embodiment of the second method for classifying fine particles of the present invention.

In the second device for classifying fine particles of the present invention, the opening 1 is not located above the classifying channel L3 in the gravitational direction (buoyant direction). Therefore, the fine particle dispersion introducing channel L1 has an angle of 0° to less than 180° with respect to a bottom surface of the classifying channel L3 in the buoyant direction (the direction opposite to the gravitational direction).

Further, in the second device for classifying fine particles of the present invention, the openings (the openings 4, 5 and 6 in the device shown in FIG. 3) of the respective recovery channels are not located below the classifying channel L3 in the gravitational direction (buoyant direction). Therefore, the recovery channels L4, L5 and L6 respectively have an angle of 0° to less than 90° with respect to a top surface of the classifying channel L3 in the buoyant direction such that their outlets are located above the classifying channel L3 in the gravitational direction (buoyant direction).

Furthermore, the classifying channel L3 and the fluid introducing channel L2 are disposed substantially horizontally (preferably horizontally) in the second device for classifying fine particles of the present invention. "Substantially horizontal" means that the angle with respect to a horizontal direction is 0° to 30°.

The second device for classifying fine particles shown in FIG. 3 includes three recovery channels and three corresponding openings, i.e., the recovery channels L4, L5 and L6 and the openings 4, 5 and 6. The number of the recovery channels, however, is not particularly limited and does not need to be three as in the device shown in FIG. 3. It is preferable that the number of the recovery channels corresponds to the number of types of fine particles to be classified.

When the second device for classifying fine particles includes multiple recovery channels, as in the device for classifying fine particles shown in FIG. 3, the recovery channels L4, L5 and L6 may be connected to the classifying channel L3 at positions of different heights in the gravitational direction (buoyant direction), at different positions thereof in a direction in which the fine particle dispersion F (or the laminar flow of the fine particle dispersion F and the fluid G) flows, or at different positions thereof in both the gravitational direction (buoyant direction) and the direction in which the fine particle dispersion F (or the laminar flow of the fine particle dispersion F and the fluid G) flows. When the recovery channels L4, L5 and L6 are connected to the classifying channel L3 at different positions thereof in the direction in which the fine particle dispersion F flows, the fine particles can be classified by using the difference in position at the top surface of the classifying channel L3 that the fine particles reach.

In the device for classifying fine particles shown in FIG. 3, the communicating portion L7 is located at the side of the classifying channel L3 opposite to the side at which the recovery channels L4, L5 and L6 are disposed. In the second device for classifying fine particles of the present invention, however, it suffices if the communicating portion L7 is located below the fluid introducing channel L2. The communicating portion L7 may be located at a rear surface of the classifying channel L3 at an upstream side thereof.

In the second device for classifying fine particles of the present invention, all of the channels except the fluid introducing channel L2 and the classifying channel L3 (i.e., the fine particle dispersion introducing channel L1 and the recovery channels L4, L5 and L6 in the device for classifying fine particles shown in FIG. 3) have an angle of ±0° to 45°, preferably ±0° to 30°, more preferably ±0° to 15°, and particularly preferably ±0° to 10°, with respect to the buoyant direction (a perpendicular line). If the angle with respect to the buoyant direction exceeds ±45°, the fine particles easily adhere to the fine particle dispersion introducing channel L1 or the recovery channels L4, L5 and L6 and may thereby block the channel.

In the device for classifying fine particles shown in FIG. 3, the fine particle dispersion introducing channel L1, the fluid introducing channel L2, the classifying channel L3 and the recovery channels L4, L5 and L6 each have a rectangular cross section. In the second device for classifying fine particles of the present invention, however, these channels do not need to necessarily have a rectangular cross section.

When the shape of the channel varies according to portions thereof, the "angle with respect to the buoyant direction" described herein refers to an angle formed by the center line of each channel and the buoyant direction.

When the second device for classifying fine particles of the present invention includes the fluid introducing channel L2 having the opening 2, the ratio of an area of the opening 1 to an area of the opening 2 (i.e., the area of the opening 1: the area of the opening 2) is preferably 0.01:1 to 1:1, and more preferably 0.05:1 to 0.5:1, in light of the relationship between the specific gravity of the dispersed fine particles and the specific gravity of the fluid, the flow rate of the fluid, and classification accuracy required.

Moreover, when the second device for classifying fine particles of the present invention includes the fluid introducing channel L2, the communicating portion L7 preferably has an inner dimension smaller than that of the classifying channel L3, as in the first device for classifying fine particles. Specifically, when, in the fine particle dispersion introducing channel L1 when viewed from below, A' is the maximum inner dimension of the communicating portion L7 in a horizontal direction orthogonal to the direction in which the fine particle dispersion F flows, and, in the classifying channel L3 when viewed below, B' is the maximum inner dimension of the classifying channel L3 in a horizontal direction orthogonal to the direction in which the laminar flow of the fine particle dispersion F and the fluid G flows, a value obtained by dividing A' by B' (A'/B') is preferably 0.949 or less, and more preferably 0.4 to 0.9. If the A'/B' exceeds 0.949, the fine particles flow extremely slow at positions extremely close to inner wall surfaces of the classifying channel L3, whereby floatation of the fine particles may become apparently fast. This may cause separation of the fine particles, which is inappropriate for the intended design of the device, and fine particles of small diameter may be mixed and recovered together with fine particles of larger diameters. When the A'/B' is below 0.4, on the other hand, the efficiency of the fine particle dispersion F introduced may deteriorate.

Further, the second device for classifying fine particles of the present invention is preferably formed so that the center line of the fine particle dispersion introducing channel L1 and the center line of the classifying channel L3 are on the same plane. When these center lines are on the same plane, an effect obtained by the A'/B' being 0.949 or less becomes more significant.

The fine particle dispersion F and the fluid G are preferably introduced with pressure through the opening 1 and the opening 2, respectively, by injection with microsyringes, rotary pumps, screw pumps, centrifugal pumps, piezopumps or the like.

The flow rate of the fine particle dispersion F in the fine particle dispersion introducing channel L1 is preferably 0.001 to 100 ml/hour, and more preferably 0.01 to 50 ml/hour.

Further, the flow rate of the fluid G in the fluid introducing channel L2 is preferably 0.002 to 1000 ml/hour, and more preferably 0.1 to 500 ml/hour.

The microreactor used in the second device for classifying fine particles of the present invention may be formed of a material which is the same as that used in the first device for classifying fine particles.

The fine particle dispersion F used in the second method for classifying fine particles, which method is carried out by using the second device for classifying fine particles of the present invention, will now be described.

It is preferable that the fine particle dispersion F is a dispersion in which fine particles having a volume-average particle size of 1.5 to 1000 µm are dispersed in a liquid medium, and the value obtained by subtracting the value of the specific gravity of the fine particles from the value of the specific gravity of the liquid medium is 0.01 to 0.9.

The volume-average particle size of the fine particles used in the second method for classifying fine particles of the present invention is required to be from 1.5 to 1000 µm, as described above, and is preferably from 1.5 to 500 µm, more preferably from 1.5 to 200 µm, and particularly preferably from 1.5 to 50 µm. If the volume-average particle size of the fine particles used in the second method for classifying fine particles of the present invention is more than 1000 µm, the fine particles in the fine particle dispersion F delivered in the microchannel suitably used in the for classifying fine particles of the present invention may block the channel since the average cross-sectional area of the microchannels is from several micrometers to several thousands of micrometers as described above. Further, if the floatation speed of the fine particles is too fast, the fine particles may adhere to an upper wall surface of the channel and block the channel due to the friction of the fine particles. On the other hand, if the volume-average particle size of the fine particles is less than 1.5 µm, the problem of fine particles being deposited hardly arises, but the influence of interaction between the fine particles and the inner wall surfaces increases, resulting in problems such as adhesion of the fine particles onto the inner wall surfaces.

The shape of the fine particles used in the second method for classifying fine particles of the present invention is not particularly limited. However, if the fine particles are of a needle form, and in particular if the long axis thereof is larger than ¼ of the width of the channel, the possibility that the channel gets blocked becomes high. From this perspective, the ratio of the long axis length of the fine particles to the short axis length thereof (that is, the long axis length/the short axis length) is preferably from 1 to 50, and more preferably from 1 to 20. It is desired to select the channel width appropriately in accordance with the particle size and the particle shape.

The fine particles used in the second method for classifying fine particles may be, but are not limited to, fine particles having a true specific gravity smaller than that of the liquid medium regardless of the presence of voids within the fine particles. Specific examples of such fine particles include rubber fine particles, wax fine particles, hollow particles and the like. Examples of the rubber fine particles which can be used include fine particles of nitril rubber, styrene rubber, isobutylene rubber and the like. These types of rubber can be formed into fine particles mechanically by emulsion polymerization, freeze pulverizing or cooled pulverizing.

As the wax fine particles, fine particles of resin formed by any conventionally known method using an emulsifier and a disperser, such as the method described in "Emulsifying and Dispersing Techniques, and Size Control of Polymer Fine Particles: Chapter 3", Report 1 of Research Group on Reaction Engineering, published in March, 1995 by Society of Polymer Science, Japan, may be used.

Further, wax fine particles (releasing agent) obtained by a dissolution deposition method or a gas phase evaporation method may also be used as the wax fine particles. In the former, a releasing agent is added to an appropriate solvent which is mutually soluble with the releasing agent when heated but insoluble therein at room temperature. The mixture is heated so that the releasing agent is dissolved in the solvent. Subsequently, the mixture is gradually cooled to room temperature, thereby depositing fine particles of the releasing agent. In the latter, a releasing agent is heated in inert gas such as helium and evaporated therefrom to produce particles in gas phase. Subsequently, these particles are recovered by attaching a cooled film or the like to the particles, and are then dispersed in a solvent.

Finer particles can be produced when any of the above methods is combined with a mechanical pulverizing method in which a medium or the like is used.

Examples of resins for raw materials of the wax fine particles include a low molecular weight polypropylene and a low molecular weight polyethylene as well as plant waxes such as carnauba wax, cotton wax, haze wax and rice wax, animal waxes such as beeswax and lanolin, mineral waxes such as ozokerite and selesyn, and petroleum waxes such as paraffin, microcrystalline wax and petrolatum. Examples of resins also include synthetic hydrocarbon waxes such as Fischer-Tropsch wax, in addition to the natural waxes. Of these, preferable resins for raw materials of the wax fine particles that may be used include a low molecular weight polypropylene and a low molecular weight polyethylene as well as carnauba wax and paraffin.

Inorganic and organic hollow particles may be used as the hollow particles. Preferable examples of inorganic hollow particles include silica-based, and silica/alumina-based particles. As organic hollow particles, resin-based particles are preferred. The number of voids within a particle may be one or plural. The void ratio is not particularly limited, but is preferably from 20% to 80%, and more preferably from 30% to 70%. Specific examples of inorganic hollow particles include Fillite (trade name), manufactured by Nippon Ferrite Co., Ltd., and Cenorrite (trade name), manufactured by Tomoe Engineering Co., Ltd. Examples of organic fine particles include Expancel (trade name), manufactured by Nippon Ferrite Co., Ltd., ADVAN CELL (trade name), manufactured by Sekisui Chemical Co., Ltd., SX866 (A) and SX866 (B) (trade names), manufactured by JSR Corp., and Nipol MH5055 (trade name), manufactured by Nippon Zeon Corp. Of the above hollow particles, Expancel, manufactured by Nippon Ferrite Co., Ltd., is preferably used. Thermal expansive fine particles such as Expancel DU are particularly used after expanding the particles to a desired size by suitably heating the particles.

A variety of methods are used for producing these fine particles. Particles can be produced by synthesis in a liquid medium and directly classifying the fine particles, or particles can be produced by mechanically pulverizing a bulk material and dispersing the resulting fine particles in a liquid medium. In this case, the material is usually pulverized in a liquid medium and is directly classified as such.

In cases where powder (i.e., fine particles) produced in a dry process is classified, it is necessary to disperse the powder in a liquid medium before using. The method for dispersing the dry powder in the liquid medium may be a method using a sand mill, a colloid mill, an attritor, a ball mill, a Dyno mill, a high-pressure homogenizer, an ultrasonic disperser, a co-ball mill, a roll mill or the like. At this time, it is preferable to perform the method under conditions where the primary particles are not pulverized by the dispersion process.

In the second method for classifying fine particles, the value obtained by subtracting the value of the specific gravity of the fine particles from the value of the specific gravity of the liquid medium is preferably 0.01 to 0.9, more preferably 0.01 to 0.6, and particularly preferably 0.05 to 0.3. If the difference obtained by subtracting the value of the specific gravity of the fine particles from the value of the specific gravity of the liquid medium exceeds 0.9, floatation of the fine particles may occur remarkably, which cannot be handled even with the present invention. If the difference is less than 0.01, classification accuracy may not be insufficient.

In the second method for classifying fine particles, any liquid medium may be suitably used as the liquid medium as long as the difference obtained by subtracting the value of the specific gravity of the fine particles from the value of the specific gravity of the liquid medium can be set to 0.01 to 0.9, as described above. The liquid medium which is the same as that used in the first method for classifying fine particles can be used.

In the second method for classifying fine particles of the present invention, the preferred liquid medium varies depending on the type of the fine particles. A dispersing agent such as a surfactant may be added to the liquid medium in order to improve dispersibility of the fine particles in the liquid medium.

In the second method for classifying fine particles of the present invention, preferred examples of the combinations of the fine particles and the liquid medium include combinations of polyolefin fine particles or hollow fine particles and an ion-exchange water. Preferred among these combinations is a combination of paraffin wax fine particles, carnauba wax fine particles or thermal expansive Expancel fine particles and an ion-exchange water.

In the second method for classifying fine particles of the present invention, the preferred content of the fine particles in the fine particle dispersion is the same as that of the first method for classifying particles.

In the second method for classifying fine particles of the present invention, the fluid G is a liquid containing no fine particles to be classified. In the second method for classifying fine particles, the fluid G is preferably the same as the liquid medium. Moreover, when the fluid G is different from the liquid medium, the fluid G is preferably selected from the specific examples of the liquid medium described above.

Further, a preferred range of the specific gravity of the fluid G with respect to the fine particles is the same as the preferred range of the specific gravity of the liquid medium with respect to the fine particles.

EXAMPLES

The present invention will be more specifically described by, but is not limited to, the following Examples.

Example 1

A dispersion (fine particle dispersion D1), in which 20% by mass (18.8% by volume) of styrene/acrylic resin particles (toner fine particles for electrophotography produced by an emulsion polymerization aggregation method) having a specific gravity of 1.08 and a volume-average particle size of about 6.5 µm are dispersed in water, is classified by using a device for classifying fine particles having a structure shown in FIG. 1 (i.e., a device which will be described later).

The device (microreactor) used in Example 1 is manufactured as follows.

The device used in Example 1 is manufactured by a generally known method for manufacturing a microreactor. Namely, an acrylic plate having desired grooves formed thereat by an end mill is aligned with another acrylic plate so that channels are formed therebetween, and the acrylic plates are thermally welded to each other by applying heat and pressure thereto. At this time, the depths of the grooves need to be determined in view of a decrease in dimensions of the channels due to the thermal welding. Subsequently, the acrylic plates are drilled and tapped at positions corresponding to an inlet and an outlet so that a tube from a syringe pump or the like is connected to the position corresponding to the inlet and a joint for connecting to a discharge tube or the like is attached to the position corresponding to the outlet. The dimensions of the device will be described later.

In the following dimensions, a "width" of each opening (rectangle) refers to a horizontal side extending in a direction orthogonal to the direction in which the fine particle dispersion D and the fluid E flow in the classifying channel L3. A "length" refers to a side orthogonal to the width. Further, a "longitudinal length" refers to a length between the center points of the openings (rectangles) at both sides of each channel. (The same applies to other Examples and Comparative Example which will be described later.)

Opening 1: a rectangular having a length of 140 µm and a width of 80 µm Fine particle dispersion introducing channel L1: a rectangular column having a longitudinal length of 1 cm and an angle of 45° with respect to a gravitational direction, the cross section of the column having a length of 100 µm and a width of 80 µm Opening 2: a rectangular having a length of 400 µm and a width of 100 µm Fluid introducing channel L2: a rectangular column having a longitudinal length of 3 cm and an angle of 90° with respect to the gravitational direction, the cross section of the column having a length of 400 µm and a width of 100 µm Classifying channel L3: a rectangular column having a longitudinal length of 10 cm and an angle of 90° with respect to the gravitational direction, the cross section of the column having a length of 500 µm and a width of 100 µm Recovery channel L4: a rectangular column having a longitudinal length of 2 cm and an angle of 45° with respect to the gravitational direction, the column having a rectangular surface with a length of 150 µm and a width of 100 µm connecting to the classifying channel L3, and an opening 4 which is a rectangular having a length of 150 µm and a width of 100 µm Recovery channel L5: a rectangular column having a longitudinal length of 1.7 cm and an angle of 35° with respect to the gravitational direction, the column having a rectangular surface with a length of 150 µm and a width of 100 µm connecting to the classifying channel L3, and an opening 5 which is a rectangular having a length of 105 µm and a width of 100 µm Recovery channel L6: a rectangular column having a longitudinal length of 1.6 cm and an angle of 25° with respect to the gravitational direction, the column having a rectangular surface with a length of 200 µm and a width of 100 µm connecting to the classifying channel L3, and an opening 6 which is a rectangular having a length of 90 µm and a width of 100 µm Communicating portion L7: a rectangular having a length of about 140 µm and a width of 80 µm The fine particle dispersion D1 is delivered at 0.36 ml/hour by a microsyringe into the device through the opening 1. Ion-exchange water (fluid E) is delivered at 1.44 ml/hour by a microsyringe into the device through the opening 2. As a result, a fine particle dispersion which has fine particles with a volume particle size of less than about 16 µm dispersed therein and contains few coarse granules of fine particles is obtained through the opening 4. Further, a fine particle dispersion having fine particles with a volume particle size of about 16 to 23 µm is obtained through the opening 5. Furthermore, a fine particle dispersion having fine particles with a volume particle size of more than about 23 µm is obtained through the opening 6. From these results, classification of the fine particles with high classification accuracy is confirmed. Although this classification of the fine particles is continuously carried out for about 5 hours, there are no indications of the fine particles accumulating in the channels and thereby blocking the channels. Moreover, since having no rotating mechanisms, the device has no contamination and is easy to clean. The recovery efficiency of the fine particles is almost 100%, which is excellent.

Example 2

Classification of fine particles is carried out in the same way as in Example 1 except for the following changes (1) to (3):

(1) 10% by mass (6% by volume) of a dispersion (fine particle dispersion D2) having tungsten powder A30 (produced by A.L.M.T. Corp) dispersed therein is used in place of the fine particle dispersion D1. (Although the tungsten powder A30 has a volume-average particle size of 0.7 µm, the powder also contains a fairly large amount of particles with a particle size of 0.3 μm or about 1 μm. The specific gravity of the tungsten powder A30 is 19.3.)

(2) In the recovery channels L4, L5 and L6 of the device, the lengths of the rectangular surfaces connecting to the classifying channel L3 are changed to 80 μm, 60 μm and 360 μm, respectively.

(3) The amount of the ion-exchange water delivered through the opening 2 is changed to 0.008 ml/hour.

As a result of the changes (1) to (3) being made to the classification of fine particles, almost all of tungsten powder having a volume particle size of about 0.6 to 0.8 μm is recovered through the opening 5, and tungsten powder having a volume particle size of more than 0.8 μm is obtained through the opening 6. Although this classification of the fine particles is continuously carried out for about 6 hours, there are no indications of the fine particles accumulating in the channels and thereby blocking the channels. Moreover, since having no rotating mechanisms, the device has no contamination and is easy to clean. The recovery efficiency of the fine particles is almost 100%, which is excellent.

Example 3

Classification of fine particles in the fine particle dispersion D1 is carried out in the same way as in Example 1 except that the widths of the opening 1, the fine particle dispersion introducing channel L1 and the communicating portion L7 are changed to 100 μm. As a result, a fine particle dispersion having fine particles with a volume particle size of less than about 16 μm dispersed therein is obtained through the opening 4. This fine particle dispersion is acceptable although a trace amount of coarse granules of fine particles are mixed therein. Further, a fine particle dispersion having fine particles with a volume particle size of about 16 to 23 μm dispersed therein is obtained through the opening 5. This fine particle dispersion also is acceptable although a trace amount of fine particles having a volume particle size of less than 16 μm are mixed therein. Furthermore, a fine particle dispersion having fine particles with a volume particle size of more than about 23 μm dispersed therein is obtained through the opening 6. This fine particle dispersion also is acceptable although a trace amount of fine particles having a volume particle size of 20 μm or less are mixed therein. From these results, classification of the fine particles with high classification accuracy is confirmed. Although this classification of the fine particles is continuously carried out for about 5 hours, there are no indications of the fine particles accumulating in the channels and thereby blocking the channels. Moreover, since having no rotating mechanisms, the device has no contamination and is easy to clean. The recovery efficiency of the fine particles is almost 100%, which is excellent.

Example 4

An aqeous dispersion (fine particle dispersion F1), in which 10% by volume of polyolefin fine particles (produced by NIPPON SEIRO CO., LTD. by forming paraffin wax with a melting point of 85° C. into fine particles by a Gorlin mixer) having a specific gravity of 0.90 and a volume-average particle size of about 6 μm are dispersed in water, is classified by using a device for classifying fine particles having a structure shown in FIG. 3 (i.e., the microreactor manufactured in the same way as in Example 1 and having dimensions which will be described later).

Details of the device are as follows.

Opening 1: a rectangular having a length of 140 μm and a width of 80 μm Fine particle dispersion introducing channel L1: a rectangular column having a longitudinal length of 1 cm and an angle of 45° with respect to a buoyant direction, the cross section of the column having a length of 100 μm and a width of 80 μm Opening 2: a rectangular having a length of 400 μm and a width of 100 μm Fluid introducing channel L2: a rectangular column having a longitudinal length of 3 cm and an angle of 90° with respect to the buoyant direction, the cross section of the column having a length of 400 μm and a width of 100 μm Classifying channel L3: a rectangular column having a longitudinal length of 10 cm and an angle of 90° with respect to the buoyant direction, the cross section of the column having a length of 500 μm and a width of 100 μm Recovery channel L4: a rectangular column having a longitudinal length of 2 cm and an angle of 45° with respect to the buoyant direction, the column having a rectangular surface with a length of 150 μm and a width of 100 μm connecting to the classifying channel L3, and an opening 4 which is a rectangular having a length of 150 μm and a width of 100 μm Recovery channel L5: a rectangular column having a longitudinal length of 1.7 cm and an angle of 35° with respect to the buoyant direction, the column having a rectangular surface with a length of 150 μm and a width of 100 μm connecting to the classifying channel L3, and an opening 5 which is a rectangular having a length of 105 μm and a width of 100 μm Recovery channel L6: a rectangular column having a longitudinal length of 1.6 cm and an angle of 25° with respect to the buoyant direction, the column having a rectangular surface with a length of 200 μm and a width of 100 μm connecting to the classifying channel L3, and an opening 6 which is a rectangular having a length of 90 μm and a width of 100 μm Communicating portion L7: a rectangular having a length of about 140 μm and a width of 80 μm The fine particle dispersion F1 is delivered at 0.02 ml/hour by a microsyringe into the device through the opening 1. Ion-exchange water (fluid E) is delivered at 0.18 ml/hour by a microsyringe into the device through the opening 2. As a result, a fine particle dispersion which has fine particles with a volume particle size of less than about 2.5 μm dispersed therein and contains few coarse granules of fine particles is obtained through the opening 4. Further, a fine particle dispersion having fine particles with a volume particle size of about 2.5 to 8 μm is obtained through the opening 5. Furthermore, a fine particle dispersion having fine particles with a volume particle size of more than about 8 μm is obtained through the opening 6. From these results, classification of the fine particles with high classification accuracy is confirmed. Although this classification of the fine particles is continuously carried out for about 5 hours, there are no indications of the fine particles accumulating in the channels and thereby blocking the channels. Moreover, since having no rotating mechanisms, the device has no contamination and is easy to clean. The recovery efficiency of the fine particles is almost 100%, which is excellent.

Example 5

Classification of fine particles is carried out in the same way as in Example 4 except for the following changes (1) to (3):

(1) A dispersion (fine particle dispersion F2) having 10% by volume of hollow resin fine particles (trade name: Expancel DU, manufactured by Nippon Ferrite Co., Ltd.) with a volume-average particle size of about 30 μm dispersed therein is used in place of the fine particle dispersion F1. The hollow resin fine particles are subjected to thermal expansion to thereby obtain a desired particle size. The fine particle dispersion F2 is delivered at 0.36 ml/hour by a microsyringe into the device through the opening 1.

(2) The dimensions of the device are changed as follows.

Opening 1: a rectangular having a length of 140 μm and a width of 80 μm Fine particle dispersion introducing channel L1: a rectangular column having a longitudinal length of 1 cm and an angle of 45° with respect to a buoyant direction, the cross section of the column having a length of 100 μm and a width of 80 μm Opening 2: a rectangular having a length of 900 μm and a width of 100 μm Fluid introducing channel L2: a rectangular column having a longitudinal length of 3 cm and an angle of 90° with respect to the buoyant direction, the cross section of the column having a length of 900 μm and a width of 100 μm Classifying channel L3: a rectangular column having a longitudinal length of 1 cm and an angle of 90° with respect to the buoyant direction, the cross section of the column having a length of 1000 μm and a width of 100 μm Recovery channel L4: a rectangular column having a longitudinal length of 2 cm and an angle of 45° with respect to the buoyant direction, the column having a rectangular surface with a length of 300 μm and a width of 100 μm connecting to the classifying channel L3, and an opening 4 which is a rectangular having a length of 300 μm and a width of 100 μm Recovery channel L5: a rectangular column having a longitudinal length of 1.7 cm and an angle of 35° with respect to the buoyant direction, the column having a rectangular surface with a length of 300 μm and a width of 100 μm connecting to the classifying channel L3, and an opening 5 which is a rectangular having a length of 210 μm and a width of 100 μm Recovery channel L6: a rectangular column having a longitudinal length of 1.6 cm and an angle of 25° with respect to the buoyant direction, the column having a rectangular surface with a length of 400 μm and a width of 100 μm connecting to the classifying channel L3, and an opening 6 which is a rectangular having a length of 170 μm and a width of 100 μm Communicating portion L7: a rectangular having a length of about 140 μm and a width of 80 μm (3) The amount of the ion-exchange water delivered through the opening 2 is changed to 3.24 ml/hour.

As a result of the changes (1) to (3) being made to the classification of fine particles, hollow resin fine particles with volume particle sizes of less than about 25 μm, 25 to 35 μm and more than 35 μm are obtained through the openings 4, 5 and 6, respectively. Although this classification of the fine particles is continuously carried out for about 5 hours, there are no indications of the fine particles accumulating in the channels and thereby blocking the channels. Moreover, since having no rotating mechanisms, the device has no contamination and is easy to clean. The recovery efficiency of the fine particles is almost 100%, which is excellent.

Example 6

Classification of fine particles in the fine particle dispersion F1 is carried out in the same way as in Example 4 except that the widths of the opening 1, the fine particle dispersion introducing channel L1 and the communicating portion L7 are changed to 100 μm. As a result, a fine particle dispersion having fine particles with a volume particle size of less than about 2.5 μm dispersed therein is obtained from the recovery channel L4. This fine particle dispersion is acceptable although a trace amount of coarse granules of fine particles are mixed therein. Further, a fine particle dispersion having fine particles with a volume particle size of about 2.5 to 8 μm dispersed therein is obtained from the recovery channel L5. This fine particle dispersion also is acceptable although a trace amount of fine particles having a volume particle size of less than 2.5 μm are mixed therein. Furthermore, a fine particle dispersion having fine particles with a volume particle size of more than about 8 μm dispersed therein is obtained from the recovery channel L6. This fine particle dispersion also is acceptable although a trace amount of fine particles having a volume particle size of 8 μm or less are mixed therein. From these results, classification of the fine particles is confirmed. Although this classification of the fine particles is continuously carried out for about 5 hours, there are no indications of the fine particles accumulating in the channels and thereby blocking the channels. Moreover, since having no rotating mechanisms, the device has no contamination and is easy to clean. The recovery efficiency of the fine particles is almost 100%, which is excellent.

The present invention can provide a method for classifying fine particles, which method has high classification efficiency and classification accuracy, does not cause contamination with abrasion components, and can classify fine particles in a dispersion while the dispersion flows stably. The present invention can also provide a device for classifying fine particles, which device can be continuously used for a long period of time, does not cause contamination with abrasion components and has high classification efficiency and classification accuracy.

What is claimed is:

1. A method for classifying fine particles, the method comprising:

introducing a fine particle dispersion in which fine particles are dispersed in a liquid medium into an inlet of a microchannel having the inlet and a recovery portion, the recovery portion including a plurality of recovery channels disposed at different positions in a gravitational direction; and delivering the fine particle dispersion, which has been introduced through the inlet, to the recovery portion in laminar flaw, wherein delivering the fine particle dispersion includes classifying the fine particles using a difference in sedimentation speed or floatation speed among the fine particles in the fine particle dispersion as the fine particles distributed at different heights in the gravitational direction due to the difference in sedimentation speed or floatation speed flow into the plurality of recovery channels.

2. A method for classifying fine particles according to claim 1, wherein the fine particles are selected from the group consisting of resin fine particles, inorganic fine particles, metal fine particles and ceramic fine particles.

3. A method for classifying fine particles according to claim 1, wherein the volume average particle size is in the range of from 0.1 μm to 1000 μm.

4. A method for classifying fine particles according to claim 1, wherein the content of the fine particles in the fine particle dispersion is in the range from 0.1 to 40% by volume.

5. A method for classifying fine particles, the method comprising:

introducing a fine particle dispersion in which fine particles are dispersed in a liquid medium into a first inlet of a microchannel having inlets and a recovery portion, the recovery portion including a plurality of recovery channels disposed at different positions in a gravitational direction and introducing a fluid into a second inlet of the microchannel; and delivering the fine particle dispersion and the fluid, which have been introduced through the inlets, to the recovery portion in laminar flow, such that the fine particle dispersion and the fluid contact at an interface therebetween, wherein delivering the fine particle dispersion includes classifying the fine particles using a difference in sedimentation speed or floatation speed among the fine particles in the laminar flow of the fine particle dispersion and the fluid as the fine particles distributed at different heights in the gravitational direction due to the difference in sedimentation speed or flotation speed flow into the plurality of recovery channels.

6. A method for classifying fine particles according to claim 5, wherein the fine particles are selected from the group consisting of resin fine particles, inorganic fine particles, metal fine particles and ceramic fine particles.

7. A method for classifying fine particles according to claim 5, wherein the volume average particle size is in the range of from 0.1 μm to 1000 μm.

8. A method for classifying fine particles according to claim 5, wherein the content of the fine particles in the fine particle dispersion is in the range from 0.1 to 40% by volume.

* * * * *